United States Patent [19]

Ichijima et al.

[11] Patent Number: 4,522,915
[45] Date of Patent: Jun. 11, 1985

[54] COLOR PHOTOGRAPHIC SILVER HALIDE LIGHT-SENSITIVE MATERIALS CONTAINING NOVEL MAGENTA COLOR-FORMING COUPLERS

[75] Inventors: Seiji Ichijima; Toshiyuki Watanabe, both of Kanagawa, Japan

[73] Assignee: Fuji Photo Film Co., Ltd., Kanagawa, Japan

[21] Appl. No.: 497,636

[22] Filed: May 24, 1983

[30] Foreign Application Priority Data

May 24, 1982 [JP]   Japan .................................. 57-87798

[51] Int. Cl.³ .............................................. G03C 1/46
[52] U.S. Cl. ...................................... 430/505; 430/555
[58] Field of Search ................................ 430/555, 505

[56] References Cited

U.S. PATENT DOCUMENTS

| | | | |
|---|---|---|---|
| 4,264,723 | 4/1981 | Ichijima et al. | 430/555 |
| 4,366,237 | 12/1982 | Ichijima et al. | 430/505 |
| 4,390,618 | 6/1983 | Kobayashi et al. | 430/555 |
| 4,413,054 | 11/1983 | Mitsui et al. | 430/505 |

*Primary Examiner*—J. Travis Brown
*Attorney, Agent, or Firm*—Sughrue, Mion, Zinn, Macpeak, and Seas

[57] ABSTRACT

A color photographic silver halide light-sensitive material is described. The material contains a 5-pyrazolone magenta coupler represented by the general formula (I):

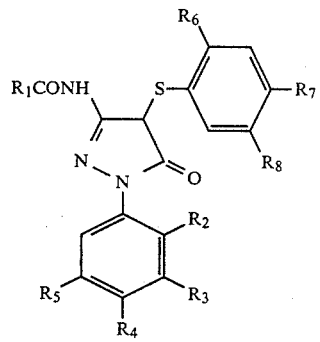

(all the symbols are as defined in the appended claims). The compounds of the general formula (I) are novel couplers, and are chemically very stable and are particularly superior in two equivalency, sensitivity, and color density.

7 Claims, No Drawings

COLOR PHOTOGRAPHIC SILVER HALIDE LIGHT-SENSITIVE MATERIALS CONTAINING NOVEL MAGENTA COLOR-FORMING COUPLERS

FIELD OF THE INVENTION

The present invention relates to color photographic silver halide light-sensitive materials containing novel magenta color-forming couplers.

BACKGROUND OF THE INVENTION

An oxidized aromatic primary amino developing agent resulting from color development of color photographic silver halide light-sensitive material which has been exposed reacts with a coupler to form a dye, producing a dye image. In this process, color reproduction is usually carried out by the subtractive color process; to reproduce blue, green, and red, color images of yellow, magenta, and cyan which are, respectively, the complementary colors thereof are formed. In general, a magenta color image is formed using a pyrazolone, cyanoacetyl, or indazolone-based coupler.

In one of the most preferred embodiments of color photographic light-sensitive material, a coupler to form a dye image is introduced into a silver halide emulsion. This coupler is itself required to be nondiffusing or is prevented from diffusing by means of an emulsion binder matrix it is placed in.

Most conventional couplers which form a magenta color image are four equivalent couplers. Since, however, the amount of silver halide required by a two equivalent coupler in the formation of a dye is only one half of that needed by a four equivalent coupler, the two equivalent coupler is advantageous over the four equivalent coupler in that rapid processing of light-sensitive material becomes possible because the thickness of a light-sensitive layer can be decreased. Photographic properties are improved by a reduction in the film thickness, and production costs are decreased. Thus, many two equivalent couplers have been developed and are disclosed in a number of patents some of which are cited below.

Various 5-pyrazolone type couplers which form a magenta color image are known. With regard to substituents at the 3-position of the 5-pyrazolone ring, an alkyl group, an aryl group, an alkoxy group as described in U.S. Pat. No. 2,439,098, a ureido group as described in U.S. Pat. No. 3,558,319, an anilino group as described in U.S. Pat. No. 2,311,081 (reissue 22,329), a dialkylamino group as described in U.S. Pat. No. 3,615,506, and an acylamino group are known.

Several attempts have been made to convert 5-pyrazolone type couplers, which have heretofore been mainly used as magenta color-forming couplers, into two equivalent ones. For example, U.S. Pat. No. 3,214,437 and 3,253,924 disclose the introduction of a thiocyano group at the 4-position of the pyrazolone ring, and furthermore, U.S. Pat. Nos. 3,311,476, 3,419,391, 3,617,291, and 3,522,052 disclose the introduction of, respectively, an acyloxy group, an aryloxy group, a 2-triazolyl group, and a halogen atom at the 4-position of the pyrazolone ring.

These 4-substituted pyrazolone couplers, however, suffer from various disadvantages; for example, they cause color fog formation, their reactivity is not suitable, they are chemically instable and change with time into substances which can not form color, and they are difficult to synthesize.

It is also known, as described in U.S. Pat. No. 3,227,554, that the 5-pyrazolone ring can be substituted by an alkylthio group, an arylthio group, or a heterocyclic thio group at the 4-position thereof. However, many of the known thio-substituted pyrazolone compounds are not suitable for use in conventional color light-sensitive materials since their reactivity with the oxidation product of an aromatic primary amino color developing agent is improper or poor, and the mercapto compounds resulting from the coupling reaction thereof have a strong photographic aciton. Furthermore, their chemical stability is insufficient.

Recently, several 5-pyrazolone two equivalent magenta couplers having a heterocyclic substituent at the 4-position thereof have been developed. For example, West German Patent Laid-Open No. 2,536,191 discloses an imidazolyl group and its derivatives, a 1,2,4-triazolyl group and its derivatives, and a 1,2,3-triazolyl group and its derivatives, and West German Patent Laid-Open No. 2,651,363 discloses a 1,2,4-triazolyl group and its derivatives.

These compounds have fairly strong color-forming properties and satisfy a part of the characteristics required for two equivalent couplers. However, they are net yet sufficiently satisfactory; for example, couplers containing a imidazolyl group or a 1,2,4-triazolyl group sometimes cause a reduction in sensitivity through the mutual action thereof with silver halide (e.g., adsorption on light-sensitive nuclei).

SUMMARY OF THE INVENTION

An object of the invention is to provide a color photographic silver halide light-sensitive material which contains a stable coupler and, therefore, even when stored for a long period of time, exhibits the same performance as just after the production thereof, and furthermore, which has good color forming properties even when used in connection with a small amount of coated silver.

Another object of the invention is to provide a color photographic light-sensitive material of high sensitivity by using a novel two equivalent magenta coupler.

Still another object of the invention is to provide a method of reducing the amount of silver halide required in a photographic emulsion layer by using a novel magenta color-forming coupler and of improving the sharpness of a color image formed.

The present inventors have found that these objects can be attained by using the novel photographic couplers represented by the general formula (I) as described hereinafter; particularly in a color photographic light-sensitive material comprising a support with at least one silver halide emulsion layer provided thereon, by incorporating the novel two equivalent magenta couplers represented by the general formula (I) into at least one silver halide emulsion layer.

The present invention relates to a color photographic silver halide light-sensitive material containing a 5-pyrazolone magenta coupler represented by the general formula (I) as described hereinafter.

DETAILED DESCRIPTION OF THE INVENTION

The magenta color-forming couplers as used herein are represented by the general formula (I):

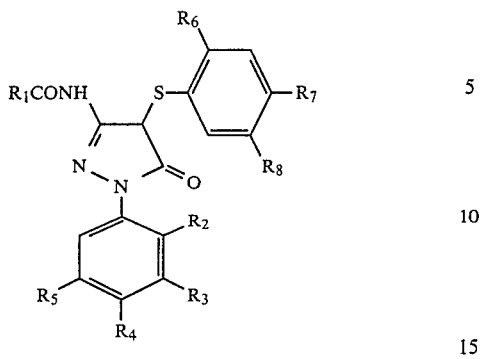

wherein $R_1$ is an ethyl group, a methyl group, a n-propyl group, a n-butyl group, a cyclopropyl group, a cyclobutyl group, an isopropyl group, an isobutyl group, or a 1-methylpropyl group, which may be substituted by an alkoxy group containing from 1 to 4 carbon atoms, an alkylthio group containing from 1 to 4 carbon atoms, a hydroxyl group, an amino group, or a halogen atom; $R_2$, $R_3$, $R_4$, and $R_5$ are each a hydrogen atom, a halogen atom, an alkyl group containing from 1 to 4 carbon atoms, an alkoxy group, an alkylthio group, an acylamino group, an alkoxycarbonyl group, an alkylaminocarbonyl group, or a dialkylaminocarbonyl group; and $R_6$, $R_7$, and $R_8$ are each a substituent selected from the group consisting of a hydrogen atom, a halogen atom, an alkyl group containing from 1 to 32 carbon atoms, an alkoxyl group, an alkylthio group, an acylamino group, an alkoxycarbonyl group, a dialkylaminocarbonyl group, an aryl group containing from 6 to 10 carbon atoms, and an amino group so that the total number of carbon atoms contained in $R_6$, $R_7$, and $R_8$ is from 8 to 32.

Of the magenta color-forming couplers of the general formula (I), those couplers in which $R_3$ is a hydrogen atom, and $R_2$, $R_4$, and $R_5$ are each a hydrogen atom, a chlorine atom, a methyl group, a methoxy group, or an acetamido group are preferably used in connection with the present invention.

In addition, those couplers in which $R_1$ is not substituted and is a methyl group, an ethyl group, a n-propyl group, a n-butyl group, an isopropyl group, an isobutyl group, or a 1-methylpropyl group are preferred.

In addition, those couplers in which $R_6$, $R_7$, and $R_8$ are substituents selected from the group consisting of an alkyl group, an alkoxyl group, an alkoxycarbonyl group, an acylamino group, and an alkylaminocarbonyl group, all containing from 1 to 20 carbon atoms, a hydrogen atom, and a chlorine atom so that the total number of carbon atoms contained in $R_6$, $R_7$, and $R_8$ is from 8 to 32 are preferred.

The couplers of the invention undergo a coupling reaction with the oxidation product of a color developing agent and, thereafter, produce mercapto compounds. These mercapto compounds, however, are nondiffusing and do not have any photographic action (e.g., an inhibition action).

Typical examples of the couplers of the invention are given below although the present invention is not limited thereto.

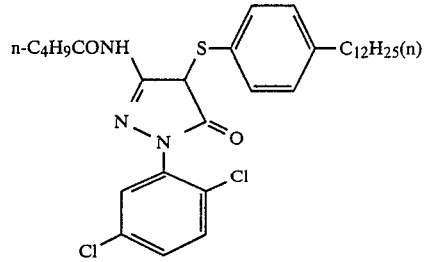

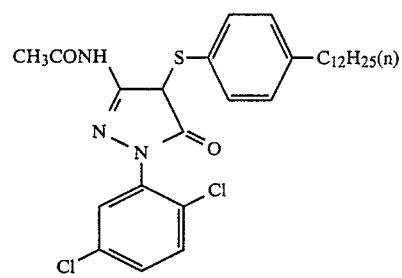

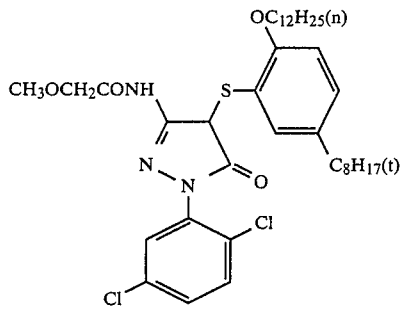

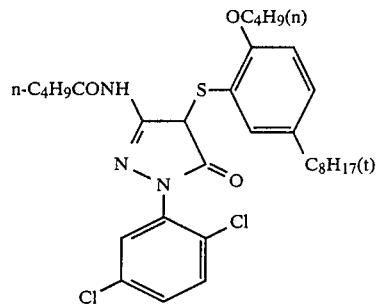

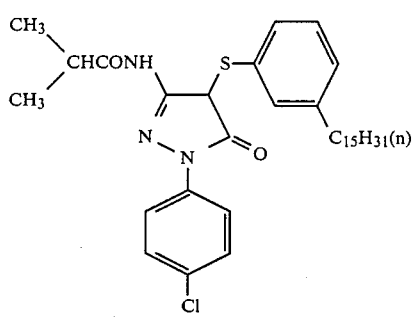

-continued
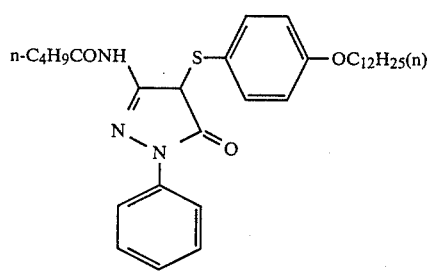 (6)
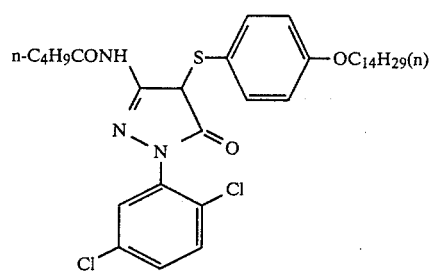 (7)
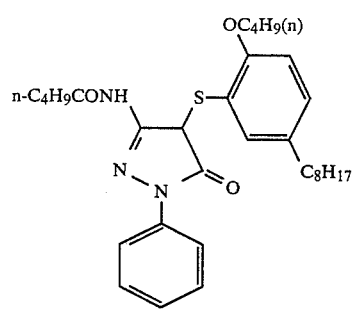 (8)
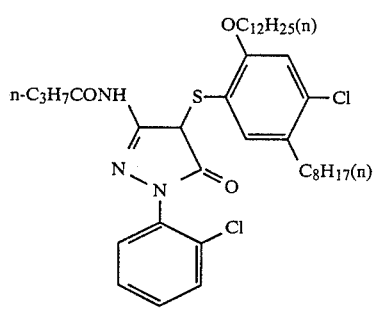 (9)
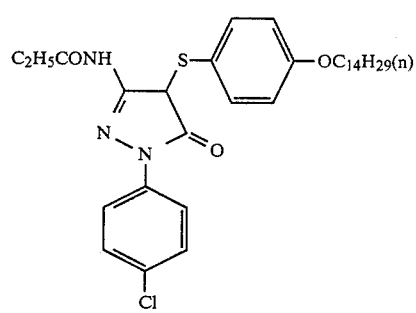 (10)
-continued
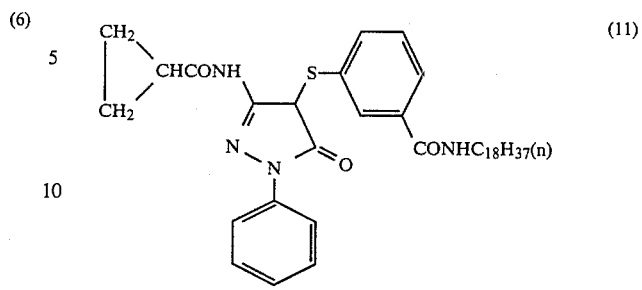 (11)
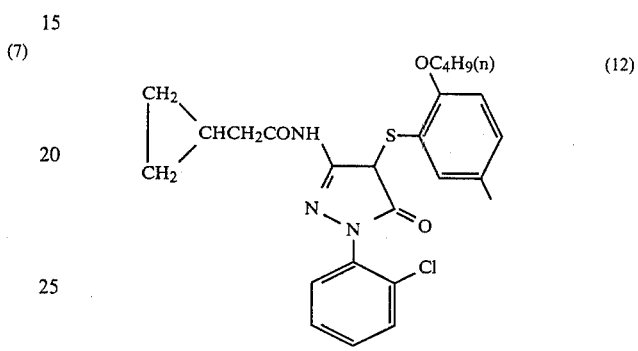 (12)
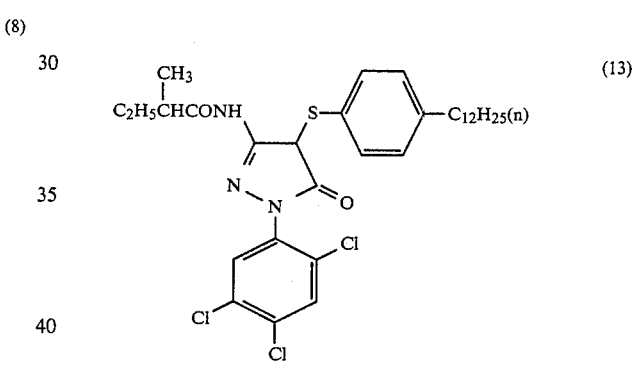 (13)
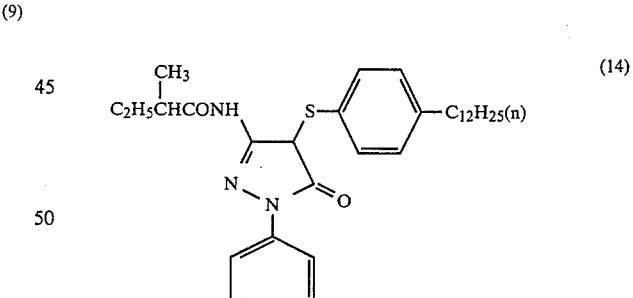 (14)
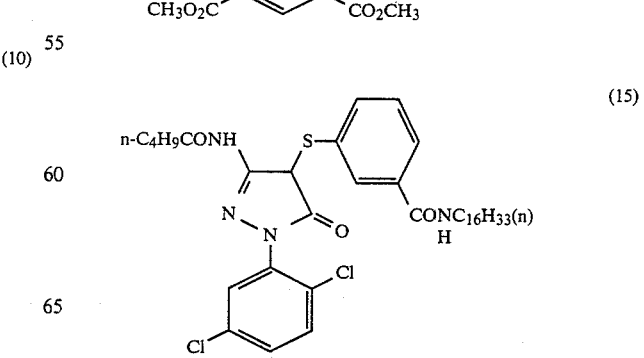 (15)

-continued

(16)
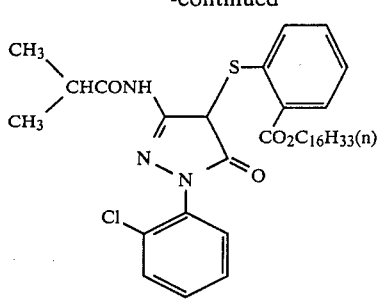

(17)
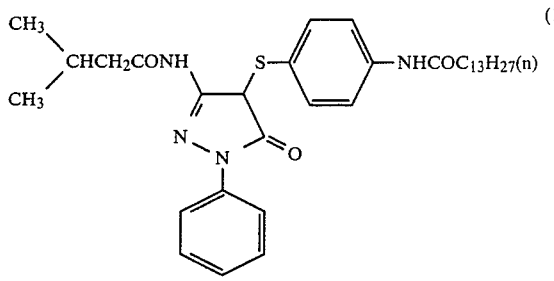

(18)
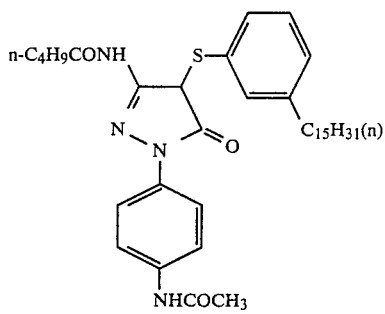

(19)
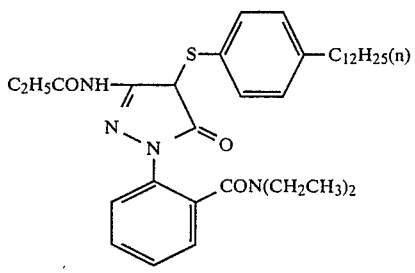

The couplers of the invention can be prepared by known procedures, e.g., the methods described in Japanese Patent Application (OPI) No. 122935/75 (corresponding to West German Patent Application (OPI) No. 2,510,538; the term "OPI" as used herein means a "published unexamined Japanese patent application"), Japanese Patent Application (OPI) No. 35858/72, and U.S. Pat. No. 3,227,554 (incorporated herein by reference to disclose methods of making the coupler).

For example, the following method can be used; that is, thiophenol derivatives or the corresponding disulfides are treated with a halogenating agent (e.g., chlorine, bromine, chlorosulfuryl, and N-bromosuccinimide) to prepare sulfenyl halides. The thus-prepared sulfenyl halides are then reacted with four equivalent couplers in the presence or absence of a base catalyst to introduce an arylthio group at a coupling active site of the couplers.

Methods of preparation of some typical compounds will hereinafter be explained. The other couplers can be synthesized by the above-described general preparation procedure.

PREPARATION EXAMPLE 1

Synthesis of Coupler (2)

4-Dodecylthiophenol (20.5 g) was dissolved in 40 ml of methylene chloride, and added dropwise to 6.5 ml of sulfuryl chloride. The resulting mixture was stirred at ordinary temperature (25° C.) for 30 minutes and, thereafter, the solvent was distilled away under reduced pressure to obtain red, oily sulfenyl chloride.

3-Acetoamido-1-(2,5-dichlorophenyl)-5-pyrazolone (20 g) was added to 100 ml of N,N-dimethylformamide, and the above-prepared sulfenyl chloride dissolved in 20 ml of methylene chloride was added thereto. The resulting mixture was stirred at 45° C. for 3 hours. At the end of the time, 100 ml of methylene chloride was added, and the mixture was washed with dilute hydrochloric acid and a saturated salt solution. An oil layer was separated and concentrated. The residue was recrystallized from a mixed solvent of acetonitrile and ethyl acetate to obtain 22.3 g of the desired coupler, m.p. 121°-124° C.

PREPARATION EXAMPLE 2

Synthesis of Coupler (7)

The procedure of Preparation Example 1 was repeated with the exception that 23.7 g of 4-tetradecyloxythiophenol was used in place of 20.5 g of 4-dodecylthiophenol, and 22.9 g of 1-(2,5-dichlorophenyl)-3-n-butanamido-5-pyrazolone was used in place of 20 g of 3-acetoamino-1-(2,5-dichlorophenyl)-5-pyrazolone.

Since the desired coupler was an oil, it was purified by column chromatography. There was thus obtained 19 g of the desired coupler.

PREPARATION EXAMPLE 3

Synthesis of Coupler (8)

S,S-Bis(2-butoxy-5-tert-octylphenyl)disulfide (19.2 g) was dissolved in 40 ml of methylene chloride, and 4.4 g of sulfuryl chloride was added thereto. The resulting mixture was stirred at 25° C. for 1 hour. At the end of the time, nitrogen was bubbled through the mixture to remove air. The thus-prepared solution was added dropwise to a solution of 16.2 g of 3-butanamido-1-phenyl-5-pyrazolone dissolved in 100 ml of N,N-dimethylformamide. After stirring at 60° C. for 2 hours, 100 ml of methylene chloride was added, and the resulting mixture was washed three times with a saturated salt solution. An oil layer was separated and concentrated. Hexane was added to the residue to obtain 29.3 g of the desired coupler, m.p. 44°-49° C.

By dissolving the couplers of the invention in any one of high boiling water-immiscible organic solvents having a boiling point of at least 170° C., low boiling organic solvents, and water-soluble organic solvents, or in high boiling water-immiscible organic solvents and/or low boiling and/or water-soluble organic solvents, they can be advantageously mixed with solvent dispersions.

All of the high boiling water-immiscible organic solvents described in U.S. Pat. No. 2,322,027 can be used as solvents. Preferred examples include di-n-butyl phthalate, benzyl phthalate, triphenyl phosphate, tri-o-cresyl phosphate, diphenyl mono-p-tert-butylphenyl phosphate, monophenyl di-o-chlorophenyl phosphate, tris(2-ethylhexyl)phosphate, dioctyl phthalate, dibutyl sebacate, acetyltributyl citrate, tri-tert-octyl trimelitate, n-nonylphenol, dioctylbutyl phosphate, N,N-diethyl-laurylamide, trihexyl phosphate, 3-pentadecyl phenyl-ethyl ether, and 2,5-di-sec-amyl phenylbutyl ether.

Low boiling organic solvents having a boiling point of 170° C. or lower, or water-soluble organic solvents which can be used in combination with high boiling solvents, or in place of the high boiling solvents are described in, for example, U.S. Pat. Nos. 2,801,171, 2,801,170, and 2,949,360.

Typical examples of such organic solvents are given below:

(1) Low boiling, substantially water-immiscible organic solvents, such as methyl acetate, ethyl acetate, propyl acetate, butyl acetate, isopropyl acetate, ethyl propionate, cyclohexanone, sec-butyl alcohol, ethyl formate, butyl formate, nitromethane, nitroethane, carbon tetrachloride, and chloroform; and (2) water-soluble organic solvents, such as methyl isobutyl ketone, β-ethoxydiethyl acetate, β-ethoxydiethyl acetate, tetrahydrofurfuryl adipate, carbitol acetate (diethylene glycol monoacetate), methoxy triglycol acetate, methylcellosolve acetate, acetylacetone, diacetone alcohol, butyl carbitol, butyl cellosolve, methyl carbitol, methyl ethyl ketone, methanol, ethanol, acetonitrile, dimethylformamide and dioxane.

The magenta couplers as used herein can be converted into azomethine dyes in high yield by an oxidative coupling reaction with exposed silver halide as an oxidizing agent. Four equivalent couplers which have heretofore been used produce leuco dyes as intermediate products for the formation of dyes, and these leuco dyes cause side reactions, such as azine ring formation, decreasing the conversion of the four equivalent couplers into the dyes. In contrast, the magenta couplers as used herein can be converted into azomethine dyes in high yield. Accordingly, in the color photographic light-sensitive material of the invention, the amount of the magenta color-forming coupler being used can be decreased. This permits a reduction in the silver halide content, a reduction in the thickness of the emulsion layer, and so forth, which will lead to a reduction in the cost of the light-sensitive material, improvements in sharpness, and acceleration of development processing.

Since the magenta couplers as used herein rapidly remove the oxidation products of developing agents being formed in the practice of color development because of their high reactivity with the oxidized aromatic primary amine color developing agents, they accelerate the development of the silver halide emulsion.

With color photographic light-sensitive materials containing the magenta couplers as used herein, the process of dye formation is completed in a color developing bath and, therefore, they can be processed in a bleach-fix bath containing a weak oxidizing agent, e.g., an EDTA iron (III) chelate, and a silver complex salt-forming agent or ferric salt (e.g., acidic ferric chloride) without the use of a bleaching bath containing a strong oxidizing agent, such as red prussiate or potassium dichromate. Accordingly, the time for all the steps of color development can be shortened, and the problem of environmental pollution due to waste water can be solved.

When the magenta couplers as used herein are used in the usual color photographic light-sensitive materials as described in the examples as illustrated hereinafter, they have good stability with time in the emulsion layer. More specifically, there is less reduction in color-forming properties with time at low temperatures and high humidities as compared with those materials containing conventional couplers. Among the most important factors for the evaluation of performance of light-sensitive material is the stability with time of the raw stock.

In addition to the above-described advantages, the magenta couplers as used herein meet the requirements generally required for the coupler. Accordingly, when their characteristics are collectively considered they are excellent couplers. For example, they produce color images which are firm and of high granularity, and when stored in the form of a raw stock, they are not subject to a reduction in coloring properties due to pollutants (e.g., formalin) in the air.

In the magenta couplers as used herein, the aryl group at the 1-position, the acylamino group at the 3-position, and the arylthio group at the 4-position of the 5-pyrazolone ring are specified, and the composition of such specific substituents produces unexpected results.

The present invention is explained in greater detail by reference to the following Examples, in which the following couplers were used as comparative couplers.

Comparative Coupler (A)

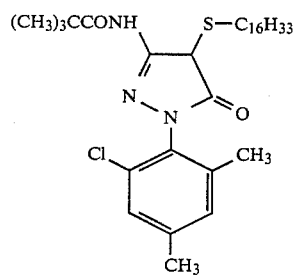

Comparative Coupler (B)

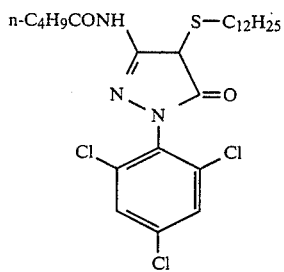

Comparative Coupler (C)

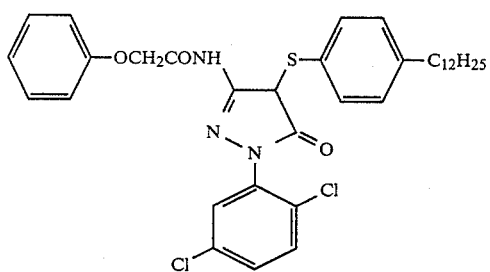

Comparative Coupler (D)

-continued

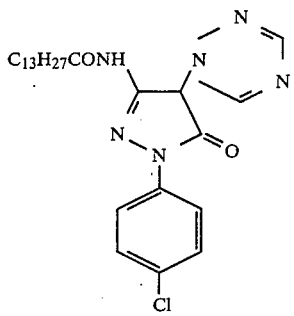

Comparative Coupler (E)

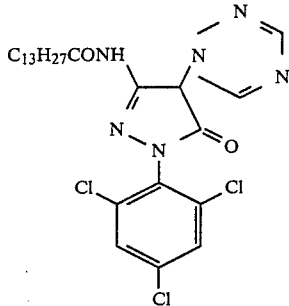

EXAMPLE 1

To 10 g of Coupler (1) of the invention were added 15 g of tricresyl phosphate and 15 ml of ethyl acetate, and Coupler (1) was dissolved therein by heating at 60° C. The resulting solution was then mixed with 100 ml of an aqueous solution containing 10 g of gelatin and 1 g of sodium dodecylbenzene sulfonate, said aqueous solution being maintained at 50° C., and stirred at a high speed by means of a homogenizer to produce a fine coupler dispersion. To the whole coupler dispersion were added a mixture of 145 g of a silver iodobromide emulsion and 7 ml of a 1% aqueous solution of 6-methyl-4-hydroxy-1,3,3a,7-tetraazaindene, said silver iodobromide emulsion containing 0.16 mole of silver and 8.7 g of gelatin and having a molar ratio of silver iodide to silver bromide of 6 to 94, and additionally, 9.5 ml of a 2% aqueous solution of sodium 2-hydroxy-4,6-dichloro-s-triazinate as a hardener to prepare a light-sensitive emulsion.

The thus-prepared light-sensitive emulsion was coated on a transparent cellulose triacetate support in an amount of $6 \times 10^{-4}$ mole/m² to produce a light-sensitive emulsion layer.

On the light-sensitive emulsion layer was coated a gelatin protective layer in an amount of 0.6 g/m² to produce a light-sensitive material, Sample (a).

In the same manner as above except that Couplers (2), (6), (10), (12), (15), and (16) of the invention were each used in place of Coupler (1), light-sensitive materials, Samples (b), (c), (d), (e), (f), and (g), respectively, were produced.

In addition, in the same manner as in the production of Sample (a) except that Comparative Couplers (A), (B), (C), (D), and (E) were each used in place of Coupler (1) of the invention, comparative light-sensitive materials, Samples (h), (i), (j), (k), and (l), respectively, were produced.

These light-sensitive materials were each exposed through an optical wedge and, thereafter, processed as follows:

| Processing Step | Temperature (°C.) | Time (minutes) |
|---|---|---|
| 1. Color Development | 38 | 3.25 |
| 2. Bleach | 38 | 6.5 |
| 3. Rinsing | 38 | 2 |
| 4. Fixing | 38 | 4 |
| 5. Rinsing | 38 | 4 |
| 6. Stabilizing Bath | 38 | 1 |

Each processing solution had the following formulation.

| Color Developer | |
|---|---|
| 4-Amino-N—ethyl-N—(β-methanesulfon-amidoethyl)aniline monosulfate | 5 g |
| Sodium sulfite | 5 g |
| Hydroxylamine sulfate | 2 g |
| Potassium carbonate | 30 g |
| Potassium hydrogencarbonate | 1.2 g |
| Potassium bromide | 1.2 g |
| Sodium chloride | 0.2 g |
| Trisodium nitrilotriacetate | 1.2 g |
| After adjustment to pH 10.1, water is added to make 1,000 ml. | |
| Bleaching Solution | |
| Iron (III) ammonium ethylene-diaminetetraacetate | 100 g |
| Disodium ethylenediaminetetraacetate | 10 g |
| Potassium bromide | 150 g |
| Glacial acetic acid | 10 g |
| After adjustment to pH 6.0, water is added to make 1,000 ml. | |
| Fixer | |
| Ammonium thiosulfate | 150 g |
| Sodium sulfite | 10 g |
| Sodium hydrogensulfite | 2.5 g |
| After adjustment to pH 6.0, water is added to make 1,000 ml. | |
| Stabilizing Bath | |
| Formalin (37%) | 5 ml |
| Fuji Driwell | 3 ml |
| Water to make | 1,000 ml |

With a magenta color image formed on each light-sensitive material, the optical density to green light was measured, and the results are shown in Table 1.

TABLE 1

| Sample | Coupler | Fog | Gamma | Maximum Density | Relative Sensitivity |
|---|---|---|---|---|---|
| a (Invention) | (1) | 0.04 | 0.58 | 1.99 | 156 |
| b (Invention) | (2) | 0.04 | 0.54 | 1.88 | 149 |
| c (Invention) | (6) | 0.04 | 0.58 | 1.98 | 157 |
| d (Invention) | (10) | 0.04 | 0.55 | 1.82 | 144 |
| e (Invention) | (12) | 0.04 | 0.52 | 1.73 | 140 |
| f (Invention) | (15) | 0.04 | 0.53 | 1.77 | 144 |
| g (Invention) | (16) | 0.04 | 0.55 | 1.73 | 149 |
| h (Comparison) | (A) | 0.05 | 0.42 | 1.53 | 100 |
| i (Comparison) | (B) | 0.04 | 0.45 | 1.54 | 107 |
| j (Comparison) | (C) | 0.05 | 0.47 | 1.65 | 112 |
| k (Comparison) | (D) | 0.04 | 0.46 | 1.61 | 70 |
| l (Comparison) | (E) | 0.04 | 0.47 | 1.63 | 72 |

Note:
(a) to (g): Examples of the invention
(h) to (l): Comparative Examples

The results of Table 1 demonstrate that the couplers of the invention provide higher sensitivity, gradation, and maximum color density than the known couplers.

By comparison between Sample (a) and Sample (i), between Sample (a) and Sample (j), and between Sample (b) and Sample (j), it can be seen that the couplers of the structure of the invention are particularly superior in respect of two equivalency, sensitivity, and color density.

It can be seen from the results of Table 1 that by changing the chlorine atom of the benzene right at the 1-position, the sensitivity of Sample (a) is greatly increased compared with Sample (i), whereas with those couplers having a triazole ring at the 4-position thereof, even if the substituent at the 1-position is changed, their sensitivities do not change; that is, the specificity of the present couplers can be understood.

EXAMPLE 2

The light-sensitive materials produced in Example 1, which had not yet been exposed, were each allowed to stand (1) at 50° C. for 2 weeks, or (2) at 5° C. for 2 weeks, were each subjected to stepwise exposure using green light, and thereafter, developed as follows:

| Processing Step | Temperature (°C.) | Time (minutes) |
|---|---|---|
| (1) Color Development | 30 | 4 |
| (2) Bleach-Fixing | 30 | 2 |
| (3) Rinsing | 30 | 2 |
| (4) Stabilization | 30 | 2 |

Color Developer

| | |
|---|---|
| Sodium metaborate | 25 g |
| Sodium sulfite | 2 g |
| Hydroxylamine (sulfuric acid salt) | 2 g |
| Potassium bromide | 0.5 g |
| 6-Nitrobenzimidazole (nitric acid salt) | 0.02 g |
| Caustic soda | 4 g |
| Diethylene glycol | 20 ml |
| 4-(N—ethyl-N—$\beta$-methanesulfonamido-aminoethyl)amino-2-methylaniline sesquisulfate | 8 g |
| Water to make | 1,000 ml |

Bleach-Fixer

| | |
|---|---|
| Ferric ethylenediaminetetraacetate | 45 g |
| Ammonium thiocyanate | 10 g |
| Sodium sulfite | 10 g |
| Ammonium thiosulfate (60% aqueous solution) | 100 ml |
| Tetrasodium ethylenediaminetetraacetate | 5 g |
| Water to make | 1,000 ml |

Stabilizing Bath

| | |
|---|---|
| Tartaric acid | 10 g |
| zinc sulfate | 10 g |
| Sodium metaborate | 20 g |
| Water to make | 1,000 ml |

With the light-sensitive materials which had been processed, the optical density was measured using green light, and the results are shown in Table 2.

TABLE 2

| Sample | Relative Color Sensitivity | | Sensitivity Reduction Rate (%) |
|---|---|---|---|
| | After allowing to stand at 5° C. for 2 weeks | After allowing to stand at 50° C for 2 weeks | |
| a | 100 | 98 | 2.0 |
| b | 93 | 90 | 3.2 |
| c | 100 | 97 | 3.0 |
| d | 93 | 90 | 3.2 |
| e | 90 | 89 | 1.1 |
| f | 94 | 91 | 2.9 |
| g | 92 | 88 | 2.8 |
| h | 67 | 52 | 22.3 |
| i | 72 | 58 | 19.4 |
| j | 75 | 70 | 6.7 |
| k | 52 | 45 | 13.5 |
| l | 56 | 51 | 8.9 | a–g present invention
h–l comparative examples

The results of Table 2 demonstrate that the couplers of the invention are very stable; even after raw stocks containing the couplers of the invention are allowed to stand in a forcedly heated condition, there is no substantial decomposition. Further, even after such storage the materials provide a color density which is nearly equal to that of a paper which is allowed to stand at a low temperature (5° C.).

EXAMPLE 3

A light-sensitive material was produced in the same manner as in Example 1 except that a mixture of 5.1 g of Coupler (7) of the invention and 5.8 g of 3-{3-(2,4-di-tert-amylphenoxy)butylamido}-benazmido-1-(2,4,6-trichlorophenyl)-2-pyrazoline-5-one was used in place of 10 g of Coupler (1) (the molar amount of the mixture was equal to that of 10 g of Coupler (1).

The thus-produced light-sensitive material, Sample (m), was processed in the same manner as in Example 2 to obtain a good photographic image.

The couplers of the invention can be used in light-sensitive materials in which the amount of silver contained in the emulsion is reduced, e.g., down to about one-hundred of that in the usual light-sensitive material.

With color photographic light-sensitive materials having such low silver contents, a color image of sufficiently high density can be produced by a developing method in which developed silver resulting from color development is subjected to halogenation bleaching, and color development is again applied to increase the amount of dye formed (see, for example, U.S. Pat. Nos. 2,623,822 and 2,814,565). It is also possible to use a method of increasing the amount of dye formed by applying, for example, an image-forming method in which color reinforcement using peroxides or cobalt complex salts is utilized (see, for example, West German Patent Application (OLS) No. 2,357,694, U.S. Pat. Nos. 3,674,490 and 3,761,265, West German Patent Application (OLS) No. 2,044,833, 2,056,359, 2,056,360, and 2,226,770, and Japanese Patent Application (OPI) Nos. 9728/73 and 9729/73), and so forth.

The couplers of the invention can be used in combination with the following compounds:

Magenta couplers as described in, for example, U.S. Pat. Nos. 2,439,098, 2,369,489, 2,600,788, 3,558,319, 2,311,081, 3,419,391, 3,214,437, 3,006,759, 2,725,292, 3,408,194, 2,908,573, 3,519,429, 3,615,506, 3,432,521, 3,152,896, 3,062,653, 3,582,322, 2,801,171, 3,311,476, British Patent No. 956,261, Japanese Patent Publication Nos. 2016/67, 19032/71, Japanese Patent Application (OPI) Nos. 74027/74, 13041/75, 131448/74, 21454/73, 60233/75, and 74028/74;

Magenta colored couplers and so-called DIR type couplers releasing compounds which inhibit imagewise development as described in, for example, U.S. Pat. Nos. 2,983,608, 2,455,170, 2,725,292, 3,005,712, 3,519,429, 2,688,539, British Pat. Nos. 800,262, 1,044,778, and Belgian Pat. No. 676,691;

Monothio type couplers as described in, for example, U.S. Pat. Nos. 3,227,550, 3,958,993, 3,227,554, 3,938,996, 4,010,035, and British Pat. No. 953,454;

o-Aminophenylazo type couplers as described in U.S. Pat. No. 3,148,062;

Couplers as described in Japanese Patent Publication No. 8750/72, West German Patent Application (OLS) Nos. 2,414,006, 2,655,871, and 2,163,811; and Hydroquinones releasing compounds which inhibit development as described in, for example, U.S. Pat. No. 3,297,445 and British Pat. No. 1,058,606.

In order to satisfy the characteristics required for light-sensitive material, two or more of the above-described couplers may be used in combination in the same layer, or the same coupler may be added to at least two layers. In general, the coupler is coated in an amount of from $1 \times 10^{-4}$ to $5 \times 10^{-3}$ mole/m² and preferably from $3 \times 10^{-4}$ to $2 \times 10^{-3}$ mole/m².

In the color photographic silver halide light-sensitive material of the invention, it is advantageous that the emulsion layer or its adjacent layer contains p-substituted phenol derivatives for the purpose of increasing the light fastness of magenta dye formed, or for preventing yellowing of couplers remaining at unexposed areas, or print out, or to present color fog formation.

Particularly effective p-substituted phenol derivatives are:

Hydroquinone derivatives as described in U.S. Pat. Nos. 2,360,290, 2,418,613, 2,675,314, 2,701,197, 2,704,713, 2,710,801, 2,728,659, 2,732,300, 2,735,765, and 2,816,038;

Gallic acid derivatives as described in U.S. Pat. Nos. 3,457,079, 3,069,262, and Japanese Patent Publication No. 13496/68;

p-Alkoxyphenols as described in U.S. Pat. No. 2,735,765, and Japanese Patent Application (OPI) No. 4738/72; and p-Oxyphenol derivatives as described in U.S. Pat. Nos. 3,432,300, 3,573,050, 3,573,627, and Japanese Patent Publication No. 20977/74.

The silver halide emulsion as used herein can be appropriately chosen from a wide variety of conventionally known emulsions depending on the purpose for which the color photographic light-sensitive material is used. Suitable examples of silver halides include silver chloride, silver chlorobromide, silver bromide, silver iodobromide, and silver chloroiodobromide. Suitable binders for use in the preparation of such silver halide emulsions include gelatin, gelatin derivatives (e.g., acylated gelatin as described in U.S. Pat. No. 3,118,766, and vinyl monomer, such as acrylic acid, grafted gelatin as described in U.S. Pat. No. 2,831,767), casein, albumin, agar, sodium alginate, starch, cellulose derivatives (e.g., carboxymethyl cellulose and hydroxyethyl cellulose), vinyl alcohol, vinyl pyrrolidone, and polyacrylamide.

These silver halide emulsions can be prepared in any suitable manner, e.g., by a single jet process, a double jet process, a controlled double jet process, and a halogen conversion process as described in, for example, British Pat. No. 635,841 and U.S. Pat. No. 3,622,318.

The silver halide emulsions may be sensitized by natural sensitizing substances existing in gelatin, sulfur sensitizing agents, reduction sensitizing agents, noble metal salts, and so on. They may contain antifoggants or stabilizers, such as 1-phenyl-5-mercaptotetrazole, and 5-methyl-7-hydroxy-1,3,4,7a-tetrazaindene. They may contain sensitizing dyes, such as cyanines and merocyanines. In addition, they may contain coating aids, such as saponin, and polyethylene glycol monolauryl ether. Furthermore, if necessary, tackifiers, e.g., polystyrenesulfonic acid, ultraviolet absorbers, e.g., 2-(2-hydroxy-3,5-di-sec-butylphenyl)-5-methoxybenzotriazole, and n-dodecyl 4-methoxy-a-cyanocinnamate, antioxidants or reducing agents, e.g., sodium hydrogensulfite, ascorbic acid, aminophenols, pyrogallol, gallic acids, catechols, resorcins, and dihydroxynaphthalenes, irradiation-preventing dyes, e.g., oxonols and styryls, and the like, which are generally used as photographic additives, may be incorporated into the silver halide emulsions.

The color photographic silver halide light-sensitive material of the invention comprises a support and at least one silver halide emulsion layer provided on the support, said silver halide emulsion layer containing the magenta coupler of the general formula (I) as described above. An preferred embodiment of the color photographic light-sensitive material of the invention is a multilayer polychromatic photographic light-sensitive material comprising a support and a blue-sensitive silver halide emulsion layer containing a yellow-forming coupler, a green-sensitive silver halide emulsion layer containing a magenta color-forming coupler of the invention, and a red-sensitive silver halide emulsion layer containing a cyan color-forming coupler provided in order on the support. In light-sensitive materials of this type, any suitable known blue-sensitive silver halide emulsions and red-sensitive silver halide emulsions can be used. Yellow color-forming couplers which are advantageously used include close chain type ketomethylene compounds exemplified by benzoylacetoanilides and pivaloylacetoanilides. Cyan color-forming couplers advantageously used include phenol-based and naphthol-based compounds. The color-forming couplers may have a coupling releasing group at the carbon atom where coupling is conducted. It is desirable for the color-forming couplers to be nondiffusing.

In the color photographic light-sensitive material of the invention, in addition to the silver halide emulsion, auxiliary light-insensitive layers, such as a protective layer, a filter layer, an intermediate layer, an antihalation layer, and a back layer, can be provided appropriately and optionally.

Hydrophilic polymeric substances, particularly gelatin contained in the layers constituting the color photographic light-sensitive material of the invention can be hardened with various kinds of cross-linking agents. Of these cross-linking agents, non aldehyde-based crosslinking agents, such as polyepoxy compounds as described in Japanese Patent Publication No. 7133/59, poly(1-aziridinyl) compounds as described in Japanese Patent Publication No. 8790/62, and active halogeno compounds as described in U.S. Pat. Nos. 3,362,827 and 3,325,287 are particularly useful, although aldehyde-based cross-linking agents, such as inorganic compounds, e.g., chromium salts and zirconium salts, mucochloric acid, and 2-phenoxy-3-chloromaleamide as described in Japanese Patent Publication No. 1872/71 can also be used.

In general, the color photographic light-sensitive material of the invention, can be produced with any conventional used for photographic light-sensitive materials. Preferred supports include cellulose ester films, such as cellulose nitrate, and cellulose acetate, polyester films, such as polyethylene terephthalate, a polyvinyl chloride film, a polyvinyl acetal film, a polystyrene film, a polycarbonate film, a polyamide film, such as nylon, a baryta paper, and an α-olefin polymer coated paper.

The color photographic light-sensitive material of the invention is used in various applications, e.g., as a color positive film, a color negative film, a color eversal film, and a color printing paper.

When the color photographic light-sensitive material of the invention is exposed imagewise by the usual procedure and, thereafter, processed according to the usual color processing process, it provides a magenta color image having excellent spectral characteristics and image fastness. Main processing steps are color development, bleach, and fixing. If necessary, between these steps, rinsing is applied.

Useful color developers are alkaline aqueous solutions containing color developing agents. As color developing agents, known aromatic primary amine dye-forming developers, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfoamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, and 4-amino-3-β-methanesulfoamidoethyl-N,N-diethylaniline, and p-aminophenols (e.g., 4-aminophenol, 2,6-dichloro-4-aminophenol, 2-bromo-4-aminophenol, and 2,6-diiodo-4-aminophenol) are used. These color developers can further contain the usual additives, such as the sulfites, carbonates, hydrogen-sulfites, bromides, and iodides of alkali metals, and alkaline buffers. Furthermore, if necessary, dye-forming couplers, competetive couplers, antifoggants, hardeners, antioxidants, tackifiers, and so forth can be added.

While the invention has been described in detail and with reference to specific embodiment thereof, it will be apparent to one skilled in the art that various changes and modifications can be made therein without departing from the spirit and scope thereof.

What is claimed is:

1. A color photographic silver halide light-sensitive material, comprising:
   a support base having positioned thereon;
   a silver halide emulsion layer, containing a silver halide dispersed within a binder and further containing a 5-pyrazolone magenta coupler represented by the general formula (I):

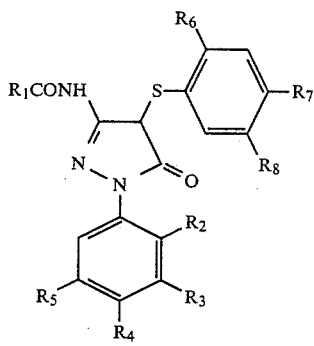

wherein $R_1$ is an ethyl group, a methyl group, a n-propyl group, a n-butyl group, a cyclopropyl group, a cyclobutyl group, an isopropyl group, an isobutyl group, or a 1-methylpropyl group, or an ethyl group, a methyl group, a n-propyl group, a n-butyl group, a cyclopropyl group, a cyclobutyl group, an isopropyl group, an isobutyl group, or a 1-methylpropyl group, which are substituted by an alkoxyl group containing from 1 to 4 carbon atoms, an alkylthio group containing from 1 to 4 carbon atoms, a hydroxyl group, an amino group, or a halogen atom; $R_2$ $R_3$, $R_4$, and $R_5$ are each a hydrogen atom, a halogen atom, an alkyl group containing from 1 to 4 carbon atoms, an alkoxy group, an alkylthio group, an acylamino group, an alkoxycarbonyl group, an alkylaminocarbonyl group, or a dialkylaminocarbonyl group; and $R_6$, $R_7$, and $R_8$ are each a substituent selected from the group consisting of a hydrogen atom, a halogen atom, an alkyl group containing from 1 to 32 carbon atoms, an alkoxy group, an alkylthio group, an acylamino group, an alkoxycarbonyl group, a dialkylaminocarbonyl group, an aryl group containing from 6 to 10 carbon atoms, and an amino group so that the total number of carbon atoms contained in $R_6$, $R_7$, and $R_8$ is from 8 to 32.

2. A color photographic silver halide light-sensitive material as claimed in claim 1, wherein $R_1$ is selected from the group consisting of a methyl group, an ethyl group, an n-propyl group, a n-butyl group, an isopropyl group, an isobutyl group, and a 1-methylpropyl group.

3. A color photographic silver halide light-sensitive material as claimed in claim 1, wherein $R_6$, $R_7$, and $R_8$ is selected from the group consisting of an alkyl group, an alkoxy group, an alkoxy carbonyl group, an acyl amino group, an alkyl amino carbonyl group, all containing 1 to 20 carbon atoms, a hydrogen atom, and a chlorine atom.

4. A color photographic silver halide light-sensitive material as claimed in claim 1, wherein the coupler of general formula (I) is present in an amount of $1 \times 10^{-4}$ to $5 \times 10^{-3}$ mole/m² of support base.

5. A color photographic silver halide light-sensitive material as claimed in claim 4, wherein the coupler of general formula (I) is present in an amount within the range of $3 \times 10^{-4}$ to $2 \times 10^{-3}$ mole/m² of support base.

6. A multi-layer polychromatic photographic light-sensitive material, comprising:
   a support base having positioned thereon;
   a blue-sensitive silver halide emulsion layer containing a yellow-forming coupler;
   a green-sensitive silver halide emulsion layer containing a magenta-forming coupler having the general formula (I); and
   a red-sensitive silver halide emulsion layer containing a cyan color-forming coupler, wherein said silver halide emulsion layers are provided in that order on the support base, wherein the magenta coupler represented by the general formula (I) is as follows:

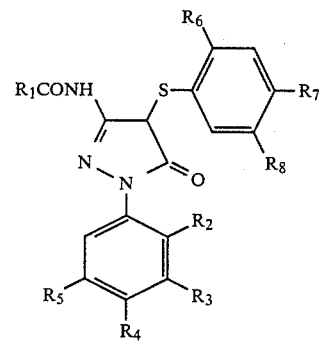

wherein $R_1$ is an ethyl group, a methyl group, a n-propyl group, a n-butyl group, a cyclopropyl group, a cyclobutyl group, an isopropyl group, an isobutyl group, or a 1-methylpropyl group, or an ethyl group, a methyl group, a n-propyl group, a n-butyl group, a cyclopropyl group, a cyclobutyl group, an isopropyl group, an isobutyl group, or a 1-methylpropyl group, which are substituted by an alkoxyl group containing from 1 to 4 carbon atoms, an alkylthio group containing from 1 to 4 carbon atoms, a hydroxyl group, an amino group, or a halogen atom; $R_2$, $R_3$, $R_4$, and $R_5$ are each a hydrogen atom, a halogen atom, an alkyl group containing from 1 to 4 carbon atoms, an alkoxy group, an alkylthio group, an acylamino group, an alkoxycarbonyl group, an alkylaminocarbonyl group, or a dialkylaminocarbonyl group; and $R_6$, $R_7$, and $R_8$ are each a substituent selected from the group consisting of a hydrogen atom, a halogen atom, an alkyl group containing from 1 to 32 carbon atoms, an alkoxy group, an alkylthio group, an acylamino group, an alkoxycarbonyl group, a dialkylaminocarbonyl group, an aryl group containing from 6 to 10 carbon atoms, and an amino group so that the total number of carbon atoms contained in $R_6$, $R_7$, and $R_8$ is from 8 to 32.

7. A multi-polychromatic photographic light-sensitive material as claimed in claim 6, wherein the coupler of the general formula (I) is present in an amount of $3 \times 10^{-4}$ to $2 \times 10^{-3}$ mole/m$^2$ of support base.

* * * * *